United States Patent [19]

Kairisalo et al.

[11] Patent Number: 5,166,437
[45] Date of Patent: Nov. 24, 1992

[54] PROCESS FOR THE PREPARATION OF FLUOXETINE

[75] Inventors: Pekka J. Kairisalo, Helsinki; Petri J. Hukka, Espoo; Anitta H. Järvinen, Helsinki, all of Finland

[73] Assignee: Orion-Yhtymä Oy, Espoo, Finland

[21] Appl. No.: 617,363

[22] Filed: Nov. 23, 1990

Related U.S. Application Data

[63] Continuation-in-part of Ser. No. 488,101, Mar. 5, 1990, abandoned, which is a continuation-in-part of Ser. No. 452,368, Dec. 19, 1989, abandoned.

[30] Foreign Application Priority Data

Mar. 3, 1989 [FI] Finland ................................ 891015

[51] Int. Cl.$^5$ .............................................. C07C 213/06
[52] U.S. Cl. ................................... 564/347; 564/342; 564/346
[58] Field of Search ......................... 564/342, 346, 347

[56] References Cited

U.S. PATENT DOCUMENTS

| | | | |
|---|---|---|---|
| 3,151,124 | 9/1964 | Huebner | 564/342 X |
| 3,642,896 | 2/1972 | Collin | 564/342 X |
| 4,296,126 | 10/1981 | Nedelec et al. | 564/346 |
| 4,314,081 | 2/1982 | Molloy et al. | 564/347 |
| 4,500,541 | 2/1985 | Hausberg et al. | 514/466 |

FOREIGN PATENT DOCUMENTS

| | | | |
|---|---|---|---|
| 535660 | 8/1985 | Spain | |
| A-2060618 | 5/1981 | United Kingdom | 564/347 |
| 2060618 | 5/1991 | United Kingdom | 564/347 |

OTHER PUBLICATIONS

Carey, *Organic Chemistry* pp. 608–609.
Fieser et al., "Reports for Organic Synthesis", vol. 1 pp. 1109–1110 (1967).
Danheisen et al. "Reports for Organic Synthesis", vol. 9, p. 381 (1981).
"Synthesis of $^{14}$C- and $^3$H- Labeled Fluoxetine, A Selective Serotonin Uptake Inhibitor", Journal of Labelled Compounds and Radiopharmaceuticals, by David W. Robertson et al., vol. 24, No. 11, 1987, John Wiley & Sons, Ltd., pp. 1397 to 1404.
The Search Report from European Application No. 90104018.8, filed Mar. 1, 1990.
"Reagents for Organic Synthesis", Fieser et al., vol. 1, pp. 1109–1110, 1967.
"Reagents for Organic Synthesis", Danheiser et al., vol. 9, p. 381, 1981.
Patent Abstracts of Japan, vol. 10, No. 239 (C-367) (2295), Aug. 19, 1986, concerning JP-A-6172736 (Toyo Soda Mfg. Ltd.), Apr. 14, 1986.
Asymmetric Synthesis of Both Enantiomers of Tomoxetine and Fluoxetine. Selective Reduction of 2,3-Epoxycinnamyl Alcohol with Red-Al, by Y. Gao and K. B. Sharpless, J. Org. Chem., vol. 53, pp. 4081–4084 (1988).

*Primary Examiner*—Marianne M. Cintins
*Assistant Examiner*—Michael B. Hydorn
*Attorney, Agent, or Firm*—Burns, Doane, Swecker & Mathis

[57] ABSTRACT

An improved process for the preparation of fluoxetine. The invention is concerned with an improved process for the preparation of the antidepressant, fluoxetine hydrochloride, or N-methyl-3-(p-trifluoromethylphenoxy)-3-phenylpropylamine hydrochloride, by simultaneous debenzylation and catalytic hydrogenation of 2-benzoyl-1-(N-benzyl-N-methyl)ethylamine base with the aid of Pd/C, Pt/C or Pd-Pt/C at a hydrogen pressure of 5 bar at 50° C. with ethyl acetate as a solvent to obtain 1-phenyl-3-(N-methylamino)-propan-1-ol. This compound is then selectively etherified with 1-chloro-4-trifluoromethylbenzene in N-methylpyrrolidone at 80° C. in the presence of potassium t-butoxide to form N-methyl-3-(p-trifluoromethylphenoxy)-3-phenylpropylamine, or fluoxetine base, which is transformed in a known manner to fluoxetine hydrochloride, or N-methyl-3-(p-trifluoromethylphenoxy)-3-phenylpropylamine hydrochloride. The yield of fluoxetine hydrochloride is 85–87% of the theoretical.

25 Claims, No Drawings

PROCESS FOR THE PREPARATION OF FLUOXETINE

This application is a continuation-in-part of U.S. Ser. No. 7/488,101 filed Mar. 5, 1990 (now abandoned), which is a continuation-in-part of U.S. Ser. No. 07/452,368, filed Dec. 19, 1989 (now abandoned).

BACKGROUND OF THE INVENTION

The invention relates to an improved process for the preparation of the antidepressant fluoxetine or N-methyl-3-(p-trifluoromethylphenoxy)-3-phenylpropylamine of formula (I),

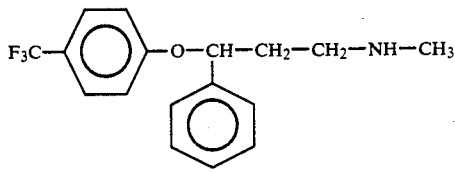

and pharmaceutically acceptable salts thereof, preferably the hydrochloride.

Fluoxetine, the pharmacological effect of which is based on its in vivo inhibiting effect on serotonin (5HT) uptake and which consequently is used as an efficient antidepressant, is a well-known compound.

Thus, the preparation of fluoxetine is earlier described, among other places, in U.S. Pat. No. 4,314,081 and in GB Patent Application No. 2,060,618, and the preparation of fluoxetine type compounds is presented in U.S. Pat. No. 4,296,126.

The object of this invention is to provide a new, more economical, safer in occupational safety and environmental protection points of view and improved process with higher yields for the production of fluoxetine.

Characteristic of the process of the present invention is, that 1-phenyl-3-(N-methylamino)propan-1-ol of formula (III)

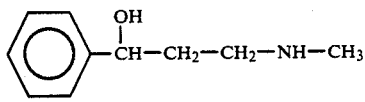

is selectively etherified with 1-chloro-4-trifluoromethylbenzene of formula (IV)

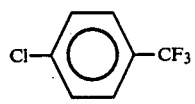

in the presence of potassium t-butoxide, resulting in fluoxetine base of formula (I) of a high purity and in good yield. The resulting base may be transformed in a known manner into a pharmaceutically acceptable salt thereof.

1-Phenyl-3-(N-methylamino)propan-1-ol of formula (III) is preferably obtained by catalytical hydrogenation and debenzylation of 2-benzoyl-1-(N-benzyl-N-methyl)ethylamine base of formula (II)

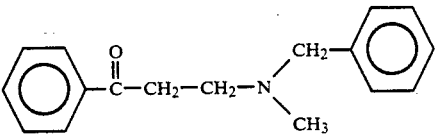

with the aid of a hydrogenation catalyst.

In the process for the preparation of fluoxetine, as in U.S. Pat. No. 4,314,081, β-dimethylaminopropiophenone hydrochloride is used as a starting material which, after the liberation of the base, is hydrogenated with diborane, $B_2H_4$. The N,N-dimethyl-3-hydroxy-3-phenylpropylamine produced in the reaction is allowed to react with thionyl chloride in chloroform containing hydrochloric acid yielding N,N-dimethyl-3-phenyl-3-chloropropylamine. This compound is allowed to react under alkaline conditions with p-trifluoro-methylphenol by heating the mixture under reflux for 5 days and nights, after which N,N-dimethyl-3-p-trifluoromethylphenoxy-3-phenylpropylamine is produced. This compound is N-demethylated with the aid of cyanogen bromide, yielding N-methyl-N-cyano-3-(p-trifuoromethylphenoxy)-phenylpropylamine. The N-cyano group is removed from this compound by heating for 20 hours at 130° C. under reflux in a mixture of potassium hydroxide and ethylene glycol. The reaction mixture is extracted with ether and the ether phase is evaporated to dryness. The residue could further be transformed in a known manner into a pharmaceutically acceptable salt of fluoxetine.

Several processes are described in GB 2,060,618, and one of them is concerned with the preparation of fluoxetine. In said process N-methyl-3-hydroxy-3-phenylpropylamine is used as a starting material, which is allowed to react with 1-fluoro-4-trifluoromethylbenzene in the presence of sodium hydride using dimethylsulfoxide as a solvent. The mixture is heated to 80° C., whereafter it is allowed to cool to room temperature. The oily residue is poured on a mixture of ice and water, which is extracted with ether. The ether phase is dried and ether is distilled off under vacuum. The residue is dissolved in ether and ether-hydrochloric acid (g) is added whereby the hydrochloride salt of fluoxetine is precipitated. The precipitate is filtered, washed with ether and dried under vacuum.

The etherification of 1-phenyl-3-(N,N-dialkylamino)-propan-1-ol type compounds with 1-halogen substituted trifluoromethylnitrobenzene is described in U.S. Pat. No. 4,296,126. This etherification reaction proceeds when an activating nitro group is attached to the phenyl ring. The reaction is carried out in the presence of sodium hydride and in a compatible solvent.

When compared with the methods mentioned before, the process according to the present invention for the preparation of fluoxetine hydrochloride is performed technically as well as economically in a more advantageous way.

In the preferred over-all method for producing of fluoxetine 1-phenyl-3-(N-methylamino)-propan-1-ol (III) is selectively etherified in the presence of potassium t-butoxide with halogen substituted p-trifluoromethylbenzene wherein the halogen may be F, Cl or Br, and the preferred reagent is 1-chloro-4-trifluoromethylbenzene. The process is carried out in an organic aprotic solvent such as N-methylpyrrolidone or dimethylsulfoxide. When using other aprotic solvents there occurs undesired side reactions, the yields are low and there appear impurities in the product. N-methylpyrrolidone is preferably used because the use of dimethylsulfoxide may produce sulfur containing waste, which is difficult to dispose of. The reaction proceeds via an alcoholate intermediate with potassium t-butoxide, which thus is not solely acting as a base. The temperature for the etherification step is generally about 20° to 200° C., preferably 80° C.

The said starting material 2-benzoyl-1-(N-benzyl-N-methyl)ethylamine base (II) is a known compound and it may be produced using methods which are in themselves known. Said base (II) is simultaneously catalytically hydrogenated and debenzylated with the aid of a hydrogenation catalyst such as Pd/C, Pt/C or Pd-Pt/C. The reaction is performed under hydrogen pressure of approximately 1–20 bar, preferably 5 bar, and at a temperature of approximately 20°–100° C., preferably 50° C., using inert solvents such as alcohols, preferably ethanol, isopropanol, 2-butanol, n-butanol, methanol and amyl alcohol, esters, preferably ethyl acetate, and butyl acetate, toluene and tetrahydrofurane. The simultaneous catalytic hydrogenation and debenzylation yields 1-phenyl-3-(N-methylamino)propan-1-ol (III).

Performed in this way, a N-methyl-3-(p-trifluoromethyl-phenoxy)-3-phenylpropylamine base in high yield is obtained, which may be transformed in a known manner in an almost theoretical yield into the corresponding hydrochloride salt (I).

The process of the present invention has several considerable advantages over the processes described earlier.

Thus, according to the process as described in U.S. Pat. No. 4,314,081, N,N-dimethylaminopropiophenone is used as a starting material, which is then after several process steps converted to N,N-dimethyl-3-p-trifluoromethylphenoxy-3-phenylpropylamine intermediate. A complicated N-demethylation step using cyanogen bromide, which is highly poisonous, tends to explode easily (Merck Index 11th ed. p. 420) and it may cause toxic impurities in the product, is performed on this intermediate, which is then further processed t yield fluoxetine.

According to the process of the invention, instead of a methyl group a benzyl group is used as a protecting group which is required in the reaction to produce compound II and thus the simultaneous debenzylation and catalytic hydrogenation of the benzylated β-aminoketone is performed and the difficult and disadvantageous demethylation can be avoided, which is a significant improvement particularly from occupational safety and environmental protection points of view. According to our knowledge this kind of simultaneous debenzylation and catalytic hydrogenation of this type of β-aminoketones has not been described in literature. Also the number of reaction steps is reduced from 6 to 3 which results in a marked increase in the total yield of the process.

The process of the present invention also has another considerable advantage over the process described in U.S. Pat. No. 4,314,081. According to the preferred embodiment of the process of the present invention, 1-phenyl-3-(N-methylamino)-propan-1-ol is allowed to react with p-chlorobenzotrifluoride. It was surprising that the etherification reaction proceeds readily with good yield using p-chlorobenzotrifluoride, because it is well known that the respective p-fluoro-compounds are much more reactive than other halides and usually activating groups such as nitro etc. are required.

According to U.S. Pat. No. 4,314,081 p-trifluoromethylphenol was heated together with N,N-dimethyl-3-phenyl-3-chloropropylamine for about 5 days in order to obtain at least some N,N-dimethyl-3-p-trifluoromethylphenoxy-3-phenylpropylamine. Moreover, the above mentioned complicated N-demethylation has to be performed on this intermediate. In the investigations which the present inventors have performed on the above mentioned process, they obtained at most a 20 yield due to the fact that the hydroxy group of p-trifluoromethylphenol reacts very poorly with the chloro substituent of N,N-dimethyl-3-phenyl-3-chloropropylamine. The process according to the invention is therefore superior from technical environmental, occupational safety and economical points of view compared to the process as described in U.S. Pat. No. 4,314,081.

In the process according to GB 2,060,618, sodium hydride is used as a reagent. Sodium hydride is very predisposed to explode, especially when it comes in contact with humidity. The reaction has thus to be performed under completely dry conditions, which is very difficult to achieve on an industrial scale.

These problems can be avoided when using potassium t-butoxide as it is described in the process of the present invention. It is significant to note that sodium hydride has been used as the reagent for production of fluoxetine and its homologs in most of the prior known processes wherein compound (III) is used as the starting material.

According to the process of the present invention, sodium hydride can be substituted with potassium-t-butoxide, the use of which is completely safe on an industrial scale.

The yield of fluoxetine hydrochloride is only 63.4 % according to the process in the examples of GB 2,060,618, when again a yield over 85 % is achieved according to the process of the present invention. Moreover, large quantities of the sodium hydride are needed for etherification, which is very hazardous for occupational safety reasons.

When comparing the process of the present invention with the process described in GB 2,060,618, it could be observed, that when etherifying 1-phenyl-3-(N-methylamino)-propan-1-ol according to the process of the present invention using p-chloro-benzotrifluoride the reaction proceeds surprisingly well and the chloro reagent is significantly cheaper than p-fluorobenzotrifluoride used in GB 2,060 618.

The process of the present invention has thus considerable technical, enonomical as well as occupational safety advantages when compared to the process as described in GB 2,060,618.

When compared with the process described in U.S. Pat. No. 4,296,126 the present invention has several advantages. The etherification reaction presented in the U.S. patent proceeds when the activating nitro group is attached to the phenyl ring, and in the reaction of the present invention no activating groups are needed. Sodium hydride, which has several disadvantages as mentioned earlier, is used as a base in the process described in the U.S. patent. In the present invention potassium t-butoxide is used and the reaction proceeds via an alcoholate intermediate and the liberation of hydrogen can thus be avoided.

In the following examples there are described several preferred embodiments to illustrate the invention.

EXAMPLE 1

1-Phenyl-3-N-methylaminopropan-1-ol 40 g (0.158 mol) of 2-benzoyl-1-(N-benzyl-N-methyl-)ethylamine was hydrogenated in an autoclave with 3–4 g Pt-Pd/C and using ethyl acetate as a solvent. The reaction was allowed to proceed for 2 hours under a hydrogen pressure of 5 bar and at a temperature of 50° C.

After the hydrogenation, the catalyst was filtered off. Ethyl acetate was distilled from the solution obtained in such a way, that the temperature of the mixture at the end is 130°–135° C. The distillation residue was allowed to cool to 70° C., whereafter 100 ml of heptane was added.

Thereafter, the mixture was cooled to −5°–−10° C. and the mixing was continued for an additional hour.

The precipitate was filtered and washed twice with 30 ml of cold heptane. The precipitate was dried under vacuum at 50° C. The yield is 22.2 g of 1-phenyl-3-N-methylaminopropan-1-ol (85% of the theoretical).

Analysis:
$^1$H-NMR (CDCl$_3$): 7.2–7.4 (multiplet 5H); 4.9 (two doublets 1H); 3.8 (singlet 2H); 2.8 (multiplet 2H) 2.4 (singlet 3H); 1.8 (multiplet 2H).

EXAMPLE 2

N-Methyl-3-(p-trifluoromethylphenoxy)-3-phenyl-propylamine 150 ml of N-methylpyrrolidone and 18.5 g (0.152 mol) of potassium t-butoxide were transferred into a N$_2$-gas secured reaction vessel and mixed for 15 minutes. To the mixture was added 25 g (0.1 52 mol) of 1-phenyl-3-N-methylaminopropan-1-ol, and 36.0 g (0.199 mol) of 1-chloro-4-trifluoromethylbenzene and mixing was continued for 6 hours at 80° C. The solution was cooled to 25° C. and 300 ml of water was added. After that, the solution was extracted twice with 200 ml of toluene. The toluene layers were combined and washed five times with 100 ml of water, and evaporated into dryness. 42 g (90% of the theoretical) of a pure N-methyl-3-(p-trifluoromethylphenoxy)-3-phenyl-propylamine base was obtained as an evaporation residue. The base was transformed in a well-known manner into fluoxetine hydrochloride in almost a quantitative yield. M.P.=154°–155° C.

Analysis:
$^1$H-NMR (CDCl$_3$) 7.4 (doublet 2H); 7.3 (multiplet 5H); 6.9 (doublet 2H); 5.3 (two doublets 1H); 2.7 (triplet 2H); 2.4 (singlet 3H); 2.2 (multiplet 1H); 2.0 (multiplet 1H); 1.4 (singlet 1H).

EXAMPLE 3

N-Methyl-3-phenyl-3-(p-trifluoromethylphenoxy)-propylamine

A mixture of 8.0 g (0.0713 mol) potassium t-butoxide, 60 ml of dimethylsufoxide, 10 g (0.0606 mol) of 1-phenyl-3-N-methylaminopropan-1-ol, and 14.8 g (0.0820 mol) of 1-chloro-4-trifluoromethylbenzene was heated to 80° C. and stirred for 4,5 hours at 80° C. The mixture was then cooled to 20°–25° C. and 80 ml of toluene and 120 ml of water were added. The layers were separated and water-phase was extracted with 80 ml of toluene. The combined toluene-phases were washed four times with 40 ml of water. Toluene was evaporated under reduced pressure yielding 18.86 g the product.

Analysis:
$^1$H-NMR (CDl$_3$): 7.4 (doublet 2H); 7.3 (multiplet 5H); 6.9 (doublet 2H); 5.3 (two doublet 1H); 2.7 (triplet 2H); 2.4 (singlet 3H); 2.2 (multiplet 1H); 2.0 (multiplet 1H); 1.4 (singlet 1H).

EXAMPLE 4

N-Methyl-3-phenyl-3-(p-trifluoromethylphenoxy)-propylamine

A mixture of 4.0 g (0.0357 mol) potassium t-butoxide, ml of N-methylpyrrolidone, 5.0 g (0.0303 mol) of 1-phenyl-3-N-methylaminopropan-1-ol, and 7.4 g (0.0410 mol) of 1-chloro-4-trifluoromethylbenzene was heated to 40° C. and stirred for 8 hours at 40° C. The mixture was then cooled to 20°–25° C. and 40 ml of toluene and water were added. The combined toluene-phases were washed four times with 20 ml of water. Toluene was evaporated under reduced pressure yielding 5.06 g of the product.

Analysis:
$^1$H-NMR (CDCl$_3$): 7.4 (doublet 2H); 7.3 (multiplet 5H); 6.9 (doublet 2H); 5.3 (two doublets 1H); 2.7 (triplet 2H); 2.4 (singlet 3H); 2.2 (multiplet 1H); 2.0 (multiplet 1H); 1.4 (singlet 1H).

EXAMPLE 5

N-Methyl-3-phenyl-3-(p-trifluoromethylphenoxy)-propylamine

A mixture of 4.0 g (0.0357 mol) potassium t-butoxide, 30 ml of N-methylpyrrolidone, 5.0 g (0.0303 mol) of 1-phenyl-3-N-methylaminopropan-1-ol and 7.4 g (0.0410 mol) of 1-chloro-4-trifluoromethylbenzene was heated to 140° C. and the reaction mixture was agitated at this temperature for 3 hours. The mixture was then cooled to 20°–25° C. and 40 ml of toluene and 60 ml of water were added. The layers were separated and water-phase was extracted with 40 ml of toluene. The combined toluene-phases were washed four times with 20 ml of water. Toluene was evaporated under reduced pressure yielding 7.19 g of the product.

Analysis:
$^1$H-NMR (CDCl$_3$): 7.4 (doublet 2H): 7.3 (multiplet 5H): 6.9 (doublet 2H); 5.3 (two doublets 1H); 2.7 (triplet 2H); 2.4 (singlet 3H); 2.2 (multiplet 1H); 2.0 (multiplet 1H); 1.4 (singlet 1H).

EXAMPLE 6

1-Phenyl-3-N-methylaminopropan-1-ol 40.0 g (0.158 mol) of 2-benzoyl-1-(N-benzyl-N-methyl)ethylamine was dissolved in 400 ml of ethyl acetate and hydrogenated with 3.0 g of Pt-Pd/C (1–4 %) catalyst at 50° C. and under 1 bar pressure. After 5.5 hours hydrogenation the catalyst was removed by filtration and ethyl acetate was evaporated under reduced pressure. After crystallization from n-heptane the yield was 19.42 g of the product.

Analysis:
$^1$H-NMR (CDCl$_3$): 7.2–7.4 (multiplet 5H); 4.9 (two doublets 1H); 3.8 (singlet 2H); 2,8 (multiplet 2H); 2.4 (singlet 3H); 1.8 (multiplet 2H).

EXAMPLE 7

1-Phenyl-3-N-methylaminopropan-1-ol 35.0 g (0.138 mol) of 2-benzoyl-1-(N-benzyl-N-methyl)ethylamine was dissolved in 350 ml of ethyl acetate and hydrogenated with 3.0 g of Pt-Pd/C (1–4

%) catalyst at 20°–25° C. and under 20 bar pressure. After 24 hours hydrogenation the catalyst was removed by filtration and ethyl acetate was evaporated under reduced pressure. After crystallization from n-heptane the yield was 11.23 g of the product.

Analysis:
¹H-NMR (CDCl₃): 7.2–7.4 (multiplet 5H); 4.9 (two doublets 1H); 3.8 (singlet 2H); 2.8 (multiplet 2H); 2.4 (singlet 3H); 1.8 (multiplet 2H).

EXAMPLE 8

1-Phenyl-3-N-methylaminopropan-1-ol 40.0 g (0.158 mol) of 2-benzoyl-1-(N-benzyl-N-methyl)-ethylamine was dissolved in 400 ml of ethyl acetate and hydrogenated with 3.0 g of Pt-Pd/C (1–4 %) catalyst at 80°–85° C. and under 8 bar pressure. After 3 hours hydrogenation the catalyst was removed by filtration and ethyl acetate was evaporated under reduced pressure. After crystallization from n-heptane the yield was 15.8 g of the the product.

Analysis:
¹H-NMR (CDCl₃): 7.2–7.4 (multiplet 5H); 4.9 (two doublets 1H); 3 8 (singlet 2H); 2.8 (multiplet 2H); 2.4 (singlet 3H); 1.8 (multiplet 2H).

We claim:

1. An improved process for the preparation in a superior yield of N-methyl-3-(p-trifluoromethylphenoxy)-3-phenylpropylamine of formula (I),

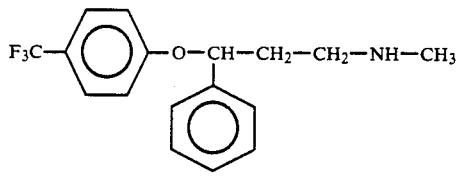

or a pharmaceutically acceptable acid addition salt thereof, the said process comprising catalytically hydrogenating 2-benzoyl-1-(N-benzyl-N-methyl)ethylamine base of formula (II),

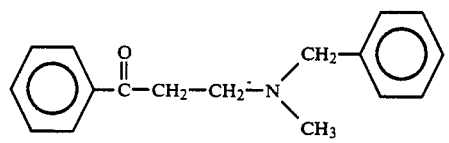

to obtain 1-phenyl-3-(N-methylamino)-propan-1-ol of formula (III),

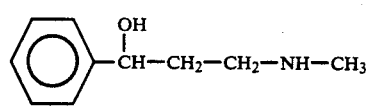

and selectively etherifying the compound of formula (III) with 1-chloro-4-trifluoromethylbenzene of formula (IV),

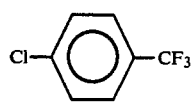

in a solvent selected from the group consisting of N-methylpyrrolidone and dimethylsulfoxide in the presence of a potassium t-butoxide, whereby N-methyl-3-(p-trifluoromethylphenoxy)-3-phenylpropylamine is formed in a yield greater than 85 percent of the theoretical value.

2. The process according to claim 1, wherein the hydrogenation of the compound of formula (II) is carried out in the presence of Pt/C, Pd/C or Pd-Pt/C catalyst.

3. The process according to claim 1, wherein the hydrogenation is carried out in the presence of water or an organic solvent.

4. The process according to claim 1, wherein the hydrogenation is carried out in the presence of ethyl acetate.

5. The process according to claim 2, wherein the hydrogenation is carried out in the presence of water or an organic solvent.

6. The process according to claim 2, wherein the hydrogenation is carried out in the presence of ethyl acetate.

7. The process according to claim 1, wherein the hydrogenation is carried out at a hydrogen pressure of 1 to 20 bar and at a temperature of approximately 20° to 100° C.

8. The process according to claim 1, wherein the hydrogenation is carried out at a hydrogen pressure of 5 bar and at a temperature of approximately 50° C.

9. The process according to claim 2, wherein the hydrogenation is carried out at a hydrogen pressure of 1 to 20 bar and at a temperature of approximately 20° to 100° C.

10. The process according to claim 2, wherein the hydrogenation is carried out at a hydrogen pressure of 5 bar and at a temperature of approximately 50° C.

11. The process according to claim 1, wherein the etherification of compound (III) is carried out in a solvent selected from the group consisting of N-methylpyrrolidone and dimethylsulfoxide at a temperature of approximately 20° to 200° C.

12. The process according to claim 1, wherein the etherification of compound (III) is carried out in a solvent selected from the group consisting of N-methylpyrrolidone and dimethylsulfoxide at a temperature of approximately 80° C.

13. The process according to claim 1, wherein the etherification of compound (III) is carried out in N-methylpyrrolidone at a temperature of approximately 20° to 200° C.

14. The process according to claim 1, wherein the etherification of compound (III) is carried out in N-methylpyrrolidone at a temperature of approximately 80° C.

15. The process according to claim 1, wherein the etherification of compound (III) is carried out in dimethylsulfoxide at a temperature of approximately 20° to 200° C.

16. The process according to claim 1, wherein the etherification of compound (III) is carried out in dimethylsulfoxide at a temperature of approximately 80° C.

17. An improved process for the preparation in a superior yield of the hydrochloride salt of N-methyl-3-(p-trifluoro-methylphenoxy)-3-phenylpropylamine of formula (I),

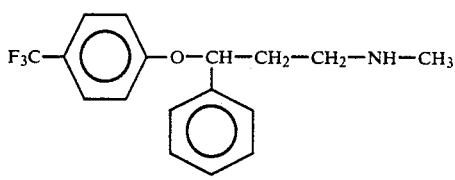

said process comprising catalytically hydrogenating 2-benzoyl-1-(N-benzyl-N-methyl)ethylamine base of formula (II),

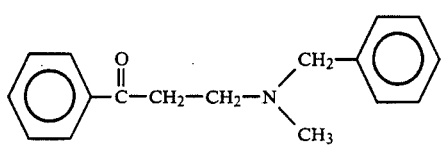

with the aid of a catalyst selected from the group consisting of Pt/C, Pd/C and Pd-Pt/C in ethyl acetate at a hydrogen pressure of 1 to 20 bar and at a temperature of approximately 20° to 100° C. whereby 1-phenyl-3-(N-methylamino)-propan-1-ol of formula (III) is formed,

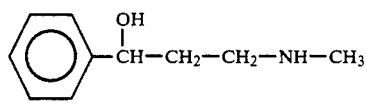

and selectively etherifying the compound of formula (III) with 1-chloro-4-trifluoromethylbenzene of formula (IV),

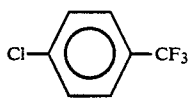

in a solvent selected from the group consisting of N-methylpyrrolidone and dimethylsulfoxide in the presence of potassium t-butoxide, whereby N-methyl-3-(p-trifluoromethylphenoxy)-3-phenylpropylamine is formed in a yield greater than 85 percent of the theoretical value and is converted to the hydrochloride salt.

18. An improved process for the production in a superior yield of N-methyl-3-(p-trifluoromethylphenoxy)-3-phenylpropylamine of the formula (I),

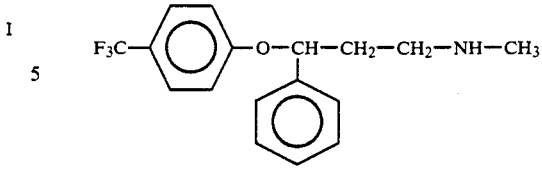

or a pharmaceutically acceptable acid addition salt thereof in which process 1-phenyl-3-(N-methylamino)-propan-1-ol of the formula (III),

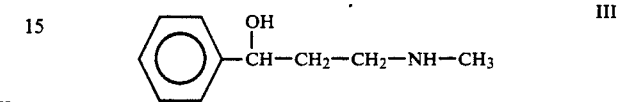

is selectively etherified with 1-chloro-4-trifluoromethylbenzene in a solvent selected from the group consisting of N-methylpyrrolidone and dimethylsulfoxide in the presence of potassium t-butoxide, whereby N-methyl-3-(p-trifluoromethylphenoxy)-3-phenylpropylamine is formed in a yield greater than 85 percent of the theoretical value.

19. A process according to claim 18 wherein the reaction is performed in a solvent selected from the group consisting of N-methylpyrrolidone and dimethylsulfoxide at a temperature of approximately 20° to 200° C.

20. A process according to claim 19 wherein the reaction is performed with 1-chloro-4-trifluoromethylbenzene in N-methylpyrrolidone at a temperature of about 80° C.

21. A process according to claim 18, wherein the 1-phenyl-3-(N-methylamino)-propan-1-ol having the formula (III) is produced by a simultaneous catalytical hydrogenation and debenzylation of 2-benzoyl-N-benzyl-N-methylethylamine of the formula (II)

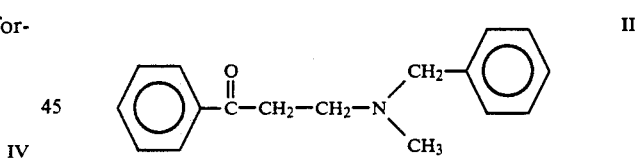

with the aid of a hydrogenation catalyst.

22. A process to claim 21 wherein the hydrogenation catalyst is selected from the group consisting of Pd/C, Pt/C and Pd-Pt/C.

23. A process according to claim 21 wherein the hydrogenation is carried out in the presence of a solvent selected from the group consisting of water and ethyl acetate.

24. A process according to claim 21 wherein the hydrogenation and debenzylation are carried out at a hydrogen pressure from about 1 bar to about 20 bar and at a temperature from about 20° C. to about 100° C.

25. A process according to claim 24 wherein the hydrogenation and debenzylation are carried out at a hydrogen pressure of about 5 bar and at a temperature of about 50° C.

* * * * *